United States Patent [19]

Kaufman

[11] 4,107,289

[45] Aug. 15, 1978

[54] USE OF SUBSTITUTED PYRANS AS DEODORANT CHEMICALS

[75] Inventor: Jerome G. Kaufman, East Norwich, N.Y.

[73] Assignee: Naarden International Holland, B.V., Naarden-Bussum, Netherlands

[21] Appl. No.: 709,668

[22] Filed: Jul. 29, 1976

Related U.S. Application Data

[63] Continuation-in-part of Ser. No. 602,958, Aug. 7, 1975, abandoned.

[51] Int. Cl.$^2$ .............................................. A61L 9/04
[52] U.S. Cl. ..................................... 424/45; 252/107; 252/522; 424/DIG. 1; 424/47; 424/61; 424/69; 424/70; 424/76; 424/283; 424/358
[58] Field of Search ..................... 424/283, 45, 47, 70, 424/358, 76, DIG. 1, 71, 65; 252/522; 260/345.7, 345.9

[56] References Cited

U.S. PATENT DOCUMENTS

| | | | |
|---|---|---|---|
| 2,898,269 | 8/1959 | Felletschin | 424/DIG. 2 |
| 2,980,703 | 4/1961 | Dunlop et al. | 424/283 X |
| 3,018,175 | 1/1962 | Cameron | 424/283 X |
| 3,030,384 | 4/1962 | Somerville | 424/283 X |
| 3,140,311 | 7/1964 | Somerville | 252/522 |
| 3,161,657 | 12/1964 | Eschenmoser et al. | 252/522 |
| 3,166,575 | 1/1965 | Nares et al. | 424/283 X |
| 3,252,998 | 5/1966 | Ohloff et al. | 252/522 X |
| 3,309,276 | 3/1967 | Cahn et al. | 252/522 X |
| 3,328,426 | 6/1967 | Ohloff | 252/522 X |
| 3,455,957 | 7/1969 | Cahn et al. | 252/522 X |
| 3,470,209 | 9/1969 | Lamparsky et al. | 252/522 X |

*Primary Examiner*—Dale R. Ore

[57] ABSTRACT

Substituted pyran compounds as exemplified by 2,5-dimethyl-3,4-dihydro-2H-pyran-2-carbinol are used as chemically active deodorizing agents in admixture with substrates such as gelatinous substances, powders, sprays, soaps, etc.

17 Claims, No Drawings

USE OF SUBSTITUTED PYRANS AS DEODORANT CHEMICALS

CROSS-REFERENCE TO RELATED APPLICATIONS

This application is a continuation-in-part of U.S. patent application Ser. No. 602,958 filed Aug. 7, 1975, now abandoned.

BACKGROUND OF THE INVENTION

1. Field of the Invention

This invention relates to the use of certain compounds as chemically active deodorizing agents. More specifically the present invention is concerned with the use of substituted pyran compounds of the type hereinafter set forth in greater detail as chemically active deodorizing agents when used in admixture with a variety of substrates.

2. Brief Description of the Prior Art

In the past, various methods and substances have been utilized for the deodorization of malodors which occur on the bodies of humans and animals and also arise in areas or spaces which have been saturated with the aforesaid malodors. These unpleasant odors or malodors may be due to smoke from cigarettes, cigars, pipes, etc.; various foodstuffs such as coffee, garlic, onion, cheeses, etc.; or other sources such as perspiration, household pets, etc. Various methods which have been used to deodorize areas such as kitchens, bathrooms, sickrooms, etc., or added directly to products, likely to emit malodors at some stage during or after their use, have included utilization of various substances which have the effect of masking or neutralizing the malodor. Another method of deodorizing areas or spaces is to use certain substances which paralyze the nerve endings associated with the sense of smell, thus rendering these nasal nerves incapable, for a certain time at least, of detecting the malodor. Yet another method of deodorizing an area is to utilize solid substances such as carbon in which the malodors are adsorbed on the surface of the solid. However, each of these methods possess certain deficiencies or drawbacks which will impair the use of the method. For example, the masking of the odor by impairing the nerve endings may produce an irritation of these nerves. Likewise, when superimposing or masking a malodor with a second odor the combination may result in producing a third odor which is more repellent to an individual than the original malodor.

In contradistinction to the above methods for removing malodors, it has now been discovered that the malodors may be destroyed in a chemical reaction by contact with certain substituted pyrans or their vapors, of a type hereinafter set forth in greater detail, these compounds being utilized as an active ingredient when admixed with the solid or gaseous substrates. The release of these vapors from the solid substrate is accomplished at varying temperatures and atmospheric pressure due to the volatility or vapor pressure of the particular substituted pyran compound which is used. These compounds can also be applied directly to the skin when used in conjunction with creams, soaps, ointments, talcum powders, hair lacquers, etc.

SUMMARY OF THE INVENTION

As hereinbefore set forth, it has now been discovered that malodors which may be present in certain areas or spaces may be destroyed by undergoing a chemical reaction with substituted pyran compounds in a liquid or vaporous state, the vapors being released from substrates at normal conditions of temperature and pressure whereby, as hereinbefore set forth, the malodor will be destroyed rather than masked by superimposing one odor which may have a more pleasant fragrance over the malodors or by paralyzing certain nasal nerve endings. By utilizing substituted pyran compounds such as a substituted dihydropyran molecule, it is possible to destroy the malodors by the formation of addition products across the double bond of the heterocyclic ring. In addition, when utilizing substituted dihydropyrans which possess a side chain containing an active double bond which is active by nature of its being alpha, beta to carbonyl groups, the activity of the compound to destroy the malodor will be significantly enhanced, thus in effect providing what may be termed as a "double-barrelled" action. This activity is particularly active against malodors in which the offensive odor is due to the presence of sulfur-containing compounds such as mercaptans, the substituted pyran being especially effective on acidic sulfur compounds.

It is therefore an object of this invention to provide substituted pyran compounds which may be utilized for the elimination of malodors.

A further object of this invention is to provide a method for the deodorization of malodors which may be found in living quarters, offices or other enclosed spaces by contacting the offensive malodors with the vapors of substituted pyran compounds which may form one component of a deodorizing composition of matter.

In one aspect an embodiment of this invention is found in the use of a compound having the formula:

wherein $R_1$ and $R_2$ are each selected from the group consisting of hydrogen, lower alkyl and cycloalkyl and R represents an organic radical; as a chemically active deodorizing agent.

A specific embodiment of this invention is found in the use of 3,4-dihydro-2H-pyran-2-carbinyl acetate or its 2,5-dimethyl homologue in admixture with a gelatinous substrate to chemically destroy malodors.

The term "lower alkyl" is used throughout the specification and claims in its usually accepted sense and is illustrated by alkyl groups having from 1 to 6 carbon atoms, inclusive, such as methyl, ethyl, propyl, butyl, pentyl, hexyl and isomeric forms thereof.

The term "cycloalkyl" is also used herein in its usually accepted sense and is illustrated by cycloalkyl having from 3 to 8 carbon atoms, inclusive, such as cyclopropyl, cyclobutyl, cyclopentyl, cyclohexyl, cycloheptyl, cyclooctyl and the like.

The term "organic radical" is used herein to mean the monovalent residue of an organic compound upon removal of a constituent group such as, for example, a hydrogen atom. The organic compound may be composed solely of atoms of carbon and hydrogen, as in the unsubstituted hydrocarbon groups, or it may contain one or more atoms of elements other than carbon and hydrogen, such as one or more atoms of oxygen, nitrogen, sulfur, halogen, etc., as in the substituted hydrocarbon groups and the heterocyclic groups.

DETAILED DESCRIPTION OF THE PREFERRED EMBODIMENTS OF THE INVENTION

The present invention is concerned with the use of compounds comprising substituted pyrans, and particularly substituted 3,4-dihydro-pyrans, as chemically active deodorizing agents. These compounds will act as chemically active deodorizing agents by destroying the malodor rather than by masking the same. In addition, the substituted dihydropyrans will not have a narcosis effect on the olfactory nervous system.

The compounds of formula (I) above and which are utilized in the present invention may be prepared by methods generally well known in the art such as that which is described in U.S. Pat. Nos. 2,479,283; 2,479,284; and 2,514,168. For example, compounds of formula (I) may be prepared by reacting alpha, beta unsaturated aldehydes or ketones with themselves or with olefinic compounds which are dissimilar in nature to the aforesaid aldehydes or ketones. The reaction may be effected in a Diels-Alder reaction by admixing the two components of the system at an elevated temperature ranging from about 100° C. to about 250° C. or more. In one method of preparing the desired product, the reaction is effected in the presence of a polymerization inhibitor which will prevent or minimize the polymerization of ethylenically unsaturated compounds, said inhibitor which is used including hydroquinone, hydroquinone monomethyl ether, quinones, etc. Generally speaking, the unsaturated aldehyde or ketone and the dissimilar olefinic compound will be present in a substantially equimolar ratio although in the event that one of the reactants possesses a tendency to polymerize more readily, it is contemplated that this component will be present in a molar excess. Another operating parameter which is utilized in preparing these compounds is pressure. Generally speaking, the reaction is preferably effected under superatmospheric pressure which is sufficient to maintain the reactants in a liquid phase, although, when utilizing higher boiling reactants and reaction products, it is possible to employ atmospheric or subatmospheric pressures. The pressure range which may be used to prepare the desired product will range from atmospheric up to about 3000 psi and preferably the pressure is maintained in a range of from about 500 psi to about 2000 psi. The particular operating pressure may be autogenous although it is also contemplated that substantially inert gases such as nitrogen may be utilized to supply the necessary pressure.

Specific examples of substituted dihydropyrans which may be employed as chemically active deodorizing agents in the present invention will include those compounds possessing one of the following general formulae:

(A) 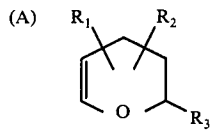 (II)

wherein $R_1$ and $R_2$ are as previously defined; $R_3$ is a moiety selected from the group consisting of those of the formulae:

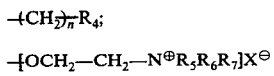

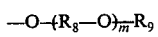

and $$-O \text{-} (R_8\text{-}O)_m R_9$$

wherein $R_4$ is a group selected from

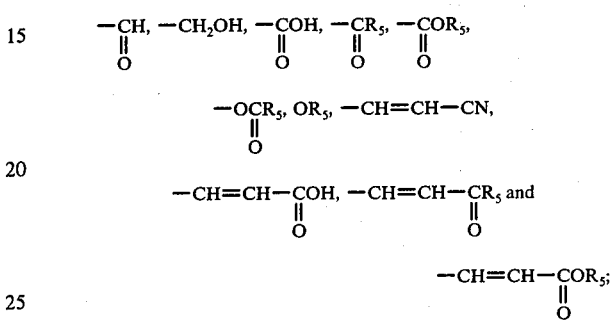

$n$ is an integer from 0 to 5, $R_5$, $R_6$ and $R_7$ are each alkyl, alkenyl, aryl, aralkyl or cycloalkyl groups with from 1 to 12 carbon atoms, inclusive; X is a halide ion, $R_8$ is a $C_2H_4$ or $C_3H_6$ alkylene group, $m$ is an integer from 1 to 10 and $R_9$ is selected from an alkyl group having 1 to 4 carbon atoms, inclusive, and a vinyl group;

(B) 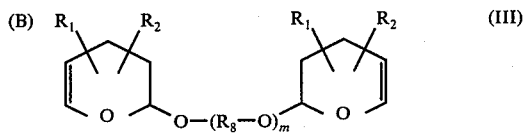 (III)

wherein $R_1$, $R_2$ and $R_8$ and $m$ are as defined above; and (C) 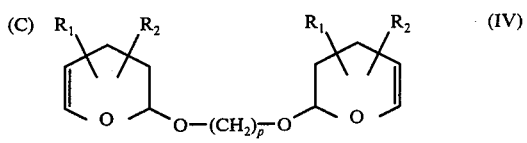 (IV)

wherein $R_1$ and $R_2$ are as defined above and $p$ is an integer of from 1 to 10. Preferred are the compounds wherein $R_1$ and $R_2$ are hydrogen or methyl. When $R_3$ is $-(CH_2)_n-R_4$ in formula (II), $n$ is preferably from 0 to 3 and $R_5$ is preferably a saturated or $\alpha$-$\beta$ unsaturated aliphatic radical. Examples of compounds within the scope of the formulae (I), (II), (III) and (IV) include (3,4-dihydro-2H-pyran-2-yl)-methanol, 2-(3,4-dihydro-2H-pyran-2-yl)-ethanol, 3-(3,4-dihydro-2H-pyran-2-yl)-propan-1-ol, 4-(3,4-dihydro-2H-pyran-2-yl)-butan-1-ol, (2-methyl-3,4-dihydro-2H-pyran-2-yl)-methanol, 2-(2-methyl-3,4-dihydro-2H-pyran-2-yl)-ethanol, 3-(2-methyl-3,4-dihydro-2H-pyran-2-yl)-propan-1-ol, 4-(2-methyl-3,4-dihydro-2H-pyran-2-yl)-butan-1-ol, (2,5-dimethyl-3,4-dihydro-2H-pyran-2-yl)-methanol, 2-(2,5-dimethyl-3,4-dihydro-2H-pyran-2-yl)-ethanol, 3-(2,5-dimethyl-3,4-dihydro-2H-pyran-2-yl)-propan-1-ol, 4-(2,5-dimethyl-3,4-dihydro-2H-pyran-2-yl)-butan-1-ol, (2-ethyl-3,4-dihydro-2H-pyran-2-yl)-methanol, 2-(2- ethyl-3,4-dihydro-2H-pyran-2-yl)-ethanol, 3-(2-ethyl-3,4-dihydro-2H-pyran-2-yl)-propan-1-ol, 4-(2-ethyl-3,4-dihydro-2H-pyran-2-yl)-butan-1-ol, (2,5-diethyl-3,4-dihydro-2H-pyran-2-yl)-methanol, 2-(2,5-diethyl-3,4-dihydro-2H-pyran-2-yl)-ethanol, 3-(2,5-diethyl-3,4-dihydro-2H-pyran-2-yl)-propan-1-ol, 4-(2,5-diethyl-3,4-dihydro-2H-pyran-2-yl)-butan-1-ol, (3,4-dihydro-2H-pyran-2-yl)-methyl acetate, (2-methyl-3,4-dihydro-2H-pyran-2-yl)-methyl acetate, (5-methyl-3,4-dihydro-2H-pyran-2-yl)-methyl acetate, (2,5-dimethyl-3,4-dihydro-2H-pyran-2-yl)-methyl acetate, (2-ethyl-3,4-dihydro-2H-pyran-2-yl)-methyl acetate, (5-ethyl-3,4-dihydro-2H-pyran-2-yl)-methyl acetate, (2,5-diethyl-3,4-dihydro-2H-pyran-2-yl)-methyl acetate, (3,4-dihydro-2H-pyran-2-yl)-methyl propionate, (2-methyl-3,4-dihydro-2H-pyran-2-yl)-methyl propionate, (5-methyl-3,4-dihydro-2H-pyran-2-yl)-methyl propionate, (2,5-dimethyl-3,4-dihydro-2H-pyran-2-yl)-methyl propionate, (2-ethyl-3,4-dihydro-2H-pyran-2-yl)-methyl propionate, (5-ethyl-3,4-dihydro-2H-pyran-2-yl)-methyl propionate, (2,5-diethyl-3,4-dihydro-2H-pyran-2-yl)-methyl propionate, (3,4-dihydro-2H-pyran-2-yl)-methyl crotonate, (2-methyl-3,4-dihydro-2H-pyran-2-yl)-methyl crotonate, (5-methyl-3,4-dihydro-2H-pyran-2-yl)-methyl crotonate, (2,5-dimethyl-3,4-dihydro-2H-pyran-2-yl)-methyl crotonate, (2-ethyl-3,4-dihydro-2H-pyran-2-yl)-methyl crotonate, (5-ethyl-3,4-dihydro-2H-pyran-2-yl)-methyl crotonate, (2,5-diethyl-3,4-dihydro-2H-pyran-2-yl)-methyl crotonate, (3,4-dihydro-2H-pyran-2-yl)-methyl senecioate, (2-methyl-3,4-dihydro-2H-pyran-2-yl)-methyl senecioate, (5-methyl-3,4-dihydro-2H-pyran-2-yl)-methyl senecioate, (2,5-dimethyl-3,4-dihydro-2H-pyran-2-yl)-methyl senecioate, (2-ethyl-3,4-dihydro-2H-pyran-2-yl)-methyl senecioate, (5-ethyl-3,4-dihydro-2H-pyran-2-yl)-methyl senecioate, (2,5-diethyl-3,4-dihydro-2H-pyran-2-yl)-methyl senecioate, 3,4-dihydro-2H-pyran-2-yl acetate, 2-methyl-3,4-dihydro-2H-pyran-2-yl acetate, 2,5-dimethyl-3,4-dihydro-2H-pyran-2-yl acetate, 2,5-diethyl-3,4-dihydro-2H-pyran-2-yl acetate, 3,4-dihydro-2H-pyran-2-yl propionate, 2-methyl-3,4-dihydro-2H-pyran-2-yl propionate, 2,5-dimethyl-3,4-dihydro-2H-pyran-2-yl propionate, 5-ethyl-3,4-dihydro-2H-pyran-2-yl propionate, 2,5-diethyl-3,4-dihydro-2H-pyran-2-yl propionate, 3,4-dihydro-2H-pyran-2-yl butyrate, 2-methyl-3,4-dihydro-2H-pyran-2-yl butyrate, 2,5-dimethyl-3,4-dihydro-2H-pyran-2-yl butyrate, 5-ethyl-3,4-dihydro-2H-pyran-2-yl butyrate, 2,5-diethyl-3,4-dihydro-2H-pyran-2-yl butyrate, 3,4-dihydro-2H-pyran-2-carboxylic acid, 2-methyl-3,4-dihydro-2H-pyran-2-carboxylic acid, 5-methyl-3,4-dihydro-2H-pyran-2-carboxylic acid, 2,5-dimethyl-3,4-dihydro-2H-pyran-2-carboxylic acid, 2-ethyl-3,4-dihydro-2H-pyran-2-carboxylic acid, 2,5-diethyl-3,4-dihydro-2H-pyran-2-carboxylic acid, 2,5-dipropyl-3,4-dihydro-2H-pyran-2-carboxylic acid, (3,4-dihydro-2H-pyran-2-yl)-acetic acid, (2-methyl-3,4-dihydro-2H-pyran-2-yl)-acetic acid, (2,5-dimethyl-3,4-dihydro-2H-pyran-2-yl)-acetic acid, 3,4-dihydro-2H-pyran-2-carboxaldehyde, 2-methyl-3,4-dihydro-2H-pyran-2-carboxaldehyde, 5-methyl-3,4-dihydro-2H-pyran-2-carboxaldehyde, 2,5-dimethyl-3,4-dihydro-2H-pyran-2-carboxaldehyde, 2-ethyl-3,4-dihydro-2H-pyran-2-carboxaldehyde, 2,5-diethyl-3,4-dihydro-2H-pyran-2-carboxaldehyde, 2,5-dipropyl-3,4-dihydro-2H-pyran-2-carboxaldehyde, (3,4-dihydro-2H-pyran-2-yl)-acetaldehyde, (2-methyl-3,4-dihydro-2H-pyran-2-yl)-acetaldehyde, (2,5-dimethyl-3,4-dihydro-2H-pyran-2-yl)-acetaldehyde, 3-(3,4-dihydro-2H-pyran-2-yl)-propanal, 3-(2-methyl-3,4-dihydro-2H-pyran-2-yl)-propanal, 3-(2,5-dimethyl-3,4-dihydro-2H-pyran-2-yl)-propanal, 1-(3,4-dihydro-2H-pyran-2-yl)-propan-2-on, 1-(2-methyl-3,4-dihydro-2H-pyran-2-yl)-propan-2-on, 1-(2,5-dimethyl-3,4-dihydro-2H-pyran-2-yl)-propan-2-on, 1-(2-ethyl-3,4-dihydro-2H-pyran-2-yl)-propan-2-on, 1-(2,5-diethyl-3,4-dihydro-2H-pyran-2-yl)-propan-2-on, 2-methoxy-3,4-dihydro-2H-pyran, 2-ethoxy-3,4-dihydro-2H-pyran, 2-ethoxy-2,5-dimethyl-3,4-dihydro-2H-pyran, 2-propoxy-3,4-dihydro-2H-pyran, 2-propoxy-2,5-dimethyl-3,4-dihydro-2H-pyran, 2-isobutoxy-3,4-dihydro-2H-pyran, 2-isobutoxy-2,5-dimethyl-3,4-dihydro-2H-pyran, 2-vinyloxy-3,4-dihydro-2H-pyran, 2-vinyloxy-2-methyl-3,4-dihydro-2H-pyran, 2-vinyloxy-2,5-dimethyl-3,4-dihydro-2H-pyran, 2-vinyloxy-2,5-diethyl-3,4-dihydro-2H-pyran, 2-isobutoxy-5-methyl-3,4-dihydro-2H-pyran, methyl 3,4-dihydro-2H-pyran-2-carboxylate, 1,2-di(3,4-dihydro-2H-pyran-2-yloxy)-ethane, 1,3-di(2,5-diethyl-3,4-dihydro-2H-pyran-2-yloxy)-propane, 1,4-di(3,4-dihydro-2H-pyran-2-yloxy)-butane. It is to be understood that the aforementioned substituted pyrans are only representative of the class of compounds which may be used, and that the present invention is not necessarily limited thereto.

As hereinbefore set forth, the substituted pyrans may be utilized to chemically destroy malodors in various ways. For example, one method of utilizing the pyrans is to composite the pyran in a gelatinous substance to form a deodorizing compound, the active ingredient thereof being the substituted pyran. The gelatinous substances which may be used as the substrate for the pyrans may be prepared by compositing a gelling agent with deionized water and adding thereto inert liquids plus other inert solids. The gelling agents which may be employed may include fatty acid soaps containing from about 10 to about 22 carbon atoms in length, the soaps including the alkali metal salts of the aforesaid acids such as sodium caprate, potassium caprate, lithium caprate, sodium laurate, potassium laurate, lithium laurate, sodium myristate, potassium myristate, lithium myristate, sodium pentadecanoate, potassium pentadecanoate, lithium pentadecanoate, sodium palmitate, potassium palmitate, sodium margarate, potassium margarate, lithium margarate, sodium stearate, potassium stearate, lithium stearate, sodium arachidate, potassium arachidate, lithium arachidate, sodium behenate, potassium behenate, lithium behenate, etc., or other compounds such as agar-agar, etc., said gelling agent being present in the finished product in an amount in the range of from about 2% to about 10% by weight of the finished composition of matter. The inert liquids which are present in the gel will include water or polyalcohols such as ethylene glycol, propylene glycol, butylene glycol, etc., said inert liquids being present in an amount in the range of from about 10% to about 93% by weight of the finished composition of matter. If so desired, it is also contemplated within the scope of this invention that the gel may include an aroma composite consisting of a mixture of aroma materials which may be present in any proportion necessary to give said composite a pleasant fragrance, said aroma materials including alcohols, aldehydes, ketones, etc., in such proportions so as to provide a perfume composition. This perfume composition may be present in a range of from about 1% or less to about 10% or more by weight of the finished composition of matter. Other inert compounds which may be present will include absorbents such as powdered silica compounds, surface active agents, etc., the inert solids being present in combined amounts ranging from about 2% to about 5% by weight of the finished product.

The amount of substituted pyran compound which may be incorporated into the gel may be varied within a wide range and will depend upon the particular application to which the gel is to be used, or upon the particular type of perfume which is incorporated into the gel. Generally speaking, the amount of substituted pyran, and particularly substituted dihydropyrans, which will possess the side chain containing a double bond which is active for purposes of destroying malodors by nature of its being alpha, beta to a carbonyl group, may range from about 0.1% to about 5% or more of the finished composition of matter. In addition, it is also contemplated within the scope of this invention that more than one substituted dihydropyran may be incorporated into the gel, the combination of pyrans which are utilized in a particular composition being selected so that the aforesaid different pyran compounds will possess different volatilities or vapor pressures thus permitting the preparation of a time-capsule type of deodorant. This type of gel deodorant thereby insures that there is a desired rate of evaporation of the pyrans into the atmosphere which will permit a continued and constant rate of evaporation to chemically destroy the malodors so that the malodors will be permanently elimited without creating any additional malodors, either from the dihydropyrans themselves or in combination with the existing malodors to be destroyed.

Another method of utilizing the dihydropyrans of the present invention for the purpose of chemically destroying malodors is to incorporate these dihydropyrans in containers such as aerosol dispensers whereby the active ingredient may be sprayed into a space which is permeated with the malodor. The composition of matter for effecting this type of deodorizing operation will comprise the dihydropyran dissolved in a solvent such as an alcohol, a glycol, or a hydrocarbon, or combinations thereof. In addition, the dihydropyran which is dissolved in the aforementioned solvent is propelled into the atmosphere by utilizing a solvent or a propellant or both. While the aforesaid discussion has been centered about a method which comprises an aerosol spray, it is also contemplated that other types of spray equipment such as atomizers or household sprayers may be used, in which case air is the customary propellant which is used. When utilizing the aerosol type of spray, the propellant which is utilized is usually gaseous under normal conditions of temperature and pressure, but is also adapted to be non-gaseous at normal temperatures by application of pressure. Specific types of propellants which may be used will include nitrogen, carbon dioxide, and the halogenated hydrocarbons of the Freon family such as trichloromonofluoromethane, dichlorodifluoromethane, etc. In addition to the dihydropyran solvent and propellant, it is also contemplated that perfume aromas may also be added to the spray dispenser so that a more desirable pleasant aroma is imparted to the atmosphere.

In addition to the use of dihydropyrans in gelatinous substances and spray dispensers, the compounds of the type hereinbefore set forth in greater detail may also be utilized as a chemically active ingredient for the destruction of malodors by incorporating the dihydropyrans in a cream base or lotion. The cream base or lotion will comprise any of the creams which are known and used in the art of cosmetics and will comprise emulsifiers such as fatty acid soaps, a specific example being sodium stearate; emollients such as lanolin which will act to soften the skin upon which the cream is used; healing agents such as allantoin which will prevent skin chapping; barrier agents such as waxes, a specific example being beeswax which will protect the skin and, if so desired, perfume compositions to impart a fragrant aroma to the cream. The dihydropyran which is to be used to destroy malodors will generally be present in the cream base in an amount in the range of from about 1 to about 30% based upon the total weight of the cream base and particularly in an amount ranging from about 2 to about 10%. In addition to the aforementioned substrates or bases in which the dihydropyrans are used, it is also contemplated that these compounds may find further use in powders —such as talcum powders, in other cosmetic preparations such as lipsticks, hair sprays or lacquers, in soaps, shampoos and other detergents for personal use, in natural or synthetic sponges or fibers etc. These compounds can be added to products which on account of their composition develop malodors (e.g. cold wave preparations), or to products that may develop malodors during their use such as certain feminine hygiene products, kitty litter and the like.

As hereinbefore set forth, substituted pyrans in which one of the substituents contains an unsaturated linkage which is alpha, beta to a carbonyl group as represented by an acid, aldehyde, ketone or ester will have what may be termed "a double-barrelled" effect on the malodors. This double action is due to the fact that these particular compounds possess two active sites, one active site being the unsaturated linkage in the heterocyclic ring of the molecule while the other active site is the unsaturated linkage on the side chain. This type of molecule will be especially effective on acidic sulfur-containing compounds such as mercaptans such as those which impart the odor of rotten eggs or amino-containing compounds which impart a fishy odor to people, articles or spaces.

The following examples are given to illustrate the use of substituted pyrans in various substrates for the chemical destruction of malodors. However, it is to be understood that these examples are given merely for purposes of illustration, and that the present invention is not to be construed in strict accordance therewith.

EXAMPLE I

In this example 2,5-dimethyl-3,4-dihydro-2H-pyran-2-carbinol is incorporated in a hair spray and a room deodorant. The hair spray is prepared by admixing 1.30 parts of resin, 0.17 parts of 2-amino-2-methyl-1,3-propanediol, 0.5 parts of lantrol, 33.23 parts of anhydrous alcohol and 65 parts of Freon. To this admixture is added 0.2% of the total fill of a 50:50 mixture of the 2,5-dimethyl-3,4 dihydro-2H-pyran-2-carbinol and a perfume composition. The room spray or deodorant is prepared by admixing 13.60 parts of anhydrous alcohol, 1.00 parts of propylene glycol, 2.40 parts of diethylene glycol and 83 parts of Freon. To this admixture is added 0.6% of the total fill of a 50:50 mixture of 2,5-dimethyl-3,4-dihydro-2H-pyran-2-carbinol and a woody-type perfume composition. The hair spray and room deodorant is then tested by spraying concentrated onion oil in a controlled smelling booth. Following this, the aforementioned hair spray and room deodorant is sprayed from an aerosol dispenser into the booth. A panel of professional fragrance evaluators determined that after a period of 0.25 hours and again after a period of 4 hours, the obnoxious odor of the onion is eliminated.

The odor which remained from the 2,5-dimethyl-3,4-dihydro-2H-pyran-2-carbinol possesses a woody or cedary character.

In like manner, a 0.2% mixture of a perfume composition and 2,5-dimethyl-3,4-dihydro-2H-pyran-2-carbinyl acetate is incorporated in a hair spray similar to that set forth in the above paragraph and 0.6% of the total fill of a 50:50 mixture of a perfume composition and 2,5-dimethyl-3,4-dihydro-1,2-pyran-2-carbinyl acetate is used in a room spray containing the same ingredients as that set forth in the above paragraph. Again concentrated onion oil is sprayed into a controlled smelling booth and thereafter the room spray and hair spray are sprayed into the booth from aerosol dispensers. A panel of professional fragrance evaluators determines that the onion odor is destroyed by the 2,5-dimethyl-3,4-dihydro-2H-pyran-2-carbinyl acetate after a period of 0.5 hours. In addition, the panel notes that the odor which remained possesses an interesting herbaceous character with the impression that it left a clean refreshing forest-like tone.

In a manner similar to that set forth in the above paragraphs, 2,5-dimethyl-3,4-dihydro-2H-pyran-2-carbinyl crotonate is used in hair spray and room deodorants or like compositions. Again concentrated onion oil is sprayed into a controlled smelling booth following which the room spray and hair spray containing the aforementioned 2,5-dimethyl-3,4-dihydro-2H-pyran-2-carbinyl crotonate is sprayed into the booth from aerosol dispensers. The panel of professional fragrance evaluators determines that a major portion of the odor is destroyed after a period of 0.25 hours and a complete elimination of the odor is effected after a period of 0.5 hours. The odor which remains from the 2,5-dimethyl-3,4-dihydro-2H-pyran-2-carbinyl crotonate is a fresh, agreeable odor.

EXAMPLE II

In this example a spray is prepared by admixing 13.3% by weight of absolute alcohol, 3.4% by weight of propylene glycol, 0.3% by phenylethoxy-3,4-dihydro-2H-pyran and 33.0% by weight of a propellant. In a manner similar to that set forth in Example I above, a malodor which possesses the odor of perspiration is sprayed into a controlled smelling booth. Following this, the spray which consists of a mixture of the ingredients hereinbefore set forth is also sprayed into the booth for a period of 4 seconds from an aerosol dispenser. After a period of 0.5 hours, a panel of professional fragrance evaluators determines that the disagreeable odor is destroyed.

When other sprays which contain 3,4-dihydro-2H-pyran-2-dodecyl ether, 3,4-dihydro-2H-pyran-2-isooctyl ether or 5-methyl-3,4-dihydro-2H-pyran-2-isobutyl ether, isooctoxy- or isobutoxy-dihydro-pyran are used, similar results are obtained, that is, the malodor of perspiration is completely destroyed and eliminated when a spray containing these various substituted dihydropyrans is introduced into the smelling booth.

EXAMPLE III

In this example an odor destroying composition of matter which contains more than one substituted dihydropyran is prepared. By admixing one or more of these substituted dihydropyrans it is possible to vary the evaporation rate of the chemically active ingredient of the deodorant so that the efficacy of said deodorant will not be impaired by a passage of time. By admixing equal amounts of 5-methyl-3,4-dihydro-2H-pyran-2-isobutyl ether and methyl-3,4-dihydro-2H-pyran-2-carboxylate it is possible to obtain a mixture whereby the evaporation rate is controlled and therefore said mixture will be suitable for the preparation of a "time-capsule" gel deodorant.

EXAMPLE IV

In this example, a mixture consisting of 10% of 2-isobutoxy-3,4-dihydro-2H-pyran, 10% of 2-isooctoxy-3,4-dihydro-2H-pyran, 40% of 2-methylisobutoxy-3,4-dihydro-2H-pyran and 40% of methyl-3,4-dihydro-2H-pyran-2-carboxylate are admixed. It is found that the evaporation rate of this mixture is sufficient for its use as a "time-capsule" deodorant. The evaporation curve of the mixture discloses that there is a very negligible amount of residue, that is, from 1 to 2%, remaining after 26 days of evaporation.

In addition to its use in gels, the mixture of substituted dihydropyrans which possessed the desirable evaporation rate is admixed with a hand cream in an amount of 0.2% by weight of the mixture. The odor destroying property of the combination of hand cream and substituted dihydropyrans is proved by rubbing onion oil on the hands of test persons followed by treatment with the hand cream. It is found that when utilizing hand creams containing the mixture of dihydropyrans, the malodors of onions and fish are removed from the hands of the test subject.

EXAMPLE V

A deodorizing gel containing the substituted dihydropyran as the chemically active ingredient thereof is prepared by adding 2% by weight of agar-agar and 0.2% by weight of a powdered silica absorbent known in the trade as Dowacil 200 to 91.5% by weight of deionized water. The mixture is mechanically agitated and heated to boiling. After reaching the boiling point, heating is discontinued and after the mixture has cooled to a temperature below 70° C., 1.3% by weight of ethylene glycol, 1.5% by weight of an anionic ethoxysulfate solubilizer known in the trade as Neocol 2040 and 0.5% by weight of a surface active agent known in the trade as Triton X-100 is added with agitation. After thoroughly admixing the solution, 0.5% by weight of 2,5-dimethyl-3,4-dihydro-2H-pyran-2-carboxaldehyde and 2.5% by weight of a perfume composition are then added to the mixture. The mixture is again thoroughly agitated and poured into a mold where, after reaching room temperature, the mixture will solidify and become a gelatinous substance.

To test the efficacy of the deodorizing gel a test is effected by spraying alpha-furfuryl mercaptan for 4 seconds from an aerosol dispenser into a controlled smelling booth, the odor of said mercaptan simulating an obnoxiously strong coffee odor. Following this, the gelatinous substance containing the 2,5-dimethyl-3,4-dihydro-2H-pyran-2-carboxaldehyde is then placed in the booth. An odor evaluation by a panel of professional fragrance evaluators will disclose the fact that the deodorizing gel containing said substituted pyran will effectively eliminate the obnoxious mercaptan odor from the booth.

EXAMPLE VI

In this example a soap is prepared by first charging an appropriate vessel with 2400 ml. of olive oil, 3800 ml. of melted tallow and 2400 ml. of coconut oil. The mixture is maintained at a temperature of about 90° C. while gently stirred. To the resulting mixture there is gradually added with stirring a mixture of 1300 mg. of pure flake lye in 3200 ml. of distilled water, the latter mixture being previously heated to a temperature of about 90° C. To the resulting mixture there is added with stirring 0.5 percent by weight of 2,5-dimethyl-3,4-dihydro-2H-pyran-2-carbinol. The soap so obtained is immediately cast into molds, covered and allowed to stand at room temperature for 24 hours. The bar soap is then removed and allowed to age for 10 days to obtain a fine grade soap useful is destroying and eliminating malodors such as mold, perspiration and like odors. The bar soap may be used as is or may be flaked or powdered by conventional methods.

What is claimed is:

1. A process for the chemical destruction of malodors imparted by compounds, by the formation of addition products across the double bond in a substituted pyran compound having the general formula:

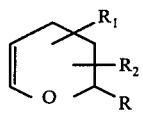

wherein $R_1$ and $R_2$ are each selected from the group consisting of hydrogen, lower alkyl and cycloalkyl and R represents an organic radical, which comprises;
providing said pyran compound in admixture with a carrier substrate; and
forming said addition products.

2. The process of claim 1 wherein the pyran compound is provided in a gelatinous substrate.

3. The process of claim 1 wherein the pyran compound is provided in admixture with a gaseous propellant.

4. The process of claim 1 wherein said pyran compound is provided in a cosmetic cream.

5. The process of claim 1 wherein the pyran compound is provided in admixture with a hair lacquer.

6. The process of claim 1 wherein the pyran compound is provided in admixture with a cold wave preparation.

7. The process of claim 1 wherein the pyran compound is provided in a soap composition.

8. The process of claim 1 wherein said pyran compound has the formula:

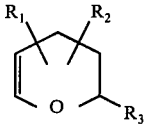

wherein $R_1$ and $R_2$ are each selected from the group consisting of hydrogen, lower alkyl and cycloalkyl and $R_3$ is a moiety selected from the group consisting of those of the formulae:

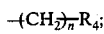

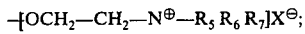

and

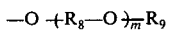

wherein $R_4$ is a group selected from

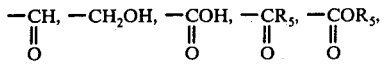

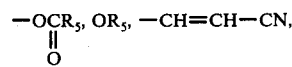

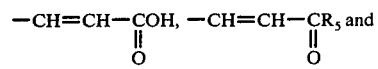

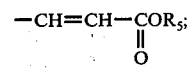

$n$ is an integer from 0 to 5, $R_5$, $R_6$ and $R_7$ are each alkyl, alkenyl, aryl, aralkyl or cycloalkyl groups with from 1 to 12 carbon atoms, inclusive; X is a halide ion, $R_8$ is a $C_2H_4$ or $C_3H_6$ alkylidene group, $m$ is an integer from 1 to 10 and $R_9$ is selected from an alkyl group having 1 to 4 carbon atoms, inclusive, and a vinyl group.

9. The process of claim 8 wherein said pyran compound is 2,5-dimethyl-3,4-dihydro-2H-pyran-2-carbinol.

10. The process of claim 8 wherein said pyran compound is 2,5-dimethyl-3,4-dihydro-2H-pyran-2-carbinyl acetate.

11. The process of claim 8 wherein said pyran compound is methyl-2,5-dimethyl-3,4-dihydro-2H-pyran-2-carboxylate.

12. The process of claim 8 wherein said pyran compound is 2,5-dimethyl-3,4-dihydro-2H-pyran-2-carboxaldehyde.

13. The process of claim 8 wherein said pyran compound is 2-isobutoxy-2,5-dimethyl-3,4-dihydro-2H-pyran.

14. The process of claim 1 wherein said pyran compound has the formula:

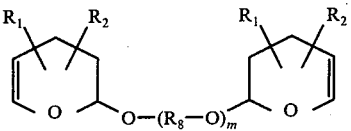

wherein $R_1$ and $R_2$ are each selected from the group consisting of hydrogen, lower alkyl and cycloalkyl, $R_8$ is selected from the group consisting of $-C_2H_4-$ and $-C_3H_6-$ and $m$ is an integer of from 1 to 10.

15. The process of claim 1 wherein said pyran compound has the formula:

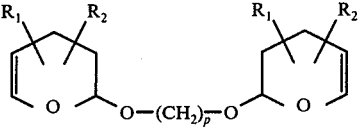

wherein $R_1$ and $R_2$ are each selected from the group consisting of hydrogen, lower alkyl and cycloalkyl and $p$ is an integer of from 1 to 10.

16. The process of claim 1 wherein the compounds associated with malodors is an acidic sulfur compound.

17. The process of claim 1 wherein the compounds associated with malodors is a mercaptan.

* * * * *